US005698515A

United States Patent [19]

Plate et al.

[11] Patent Number: 5,698,515
[45] Date of Patent: Dec. 16, 1997

[54] INSULIN-CONTAINING POLYMER COMPOSITION FOR ORAL ADMINISTRATION

[75] Inventors: Nikolai Alfredovich Plate; Lev Ivanovich Valuev; Tatyana Alexandrovna Valueva; Ljudmila Konstantinovna Staroseltseva; Alexandr Sergeevich Ametov; Vladimir Alexnadrovich Knyazhev, all of Moscow, Russian Federation

[73] Assignee: Institut Neftekhimicheskogo Sinteza Imeni A.V.Topchieva Rossiiskoi Akademii Nauk, Russian Federation

[21] Appl. No.: 408,076

[22] Filed: Mar. 22, 1995

[30] Foreign Application Priority Data

Mar. 23, 1994 [RU] Russian Federation ............ 94010864

[51] Int. Cl.$^6$ .......................... A61K 38/28; A61K 47/30
[52] U.S. Cl. ............................ 514/3; 424/487; 514/4
[58] Field of Search .................... 530/303; 525/54.1; 514/3, 4, 866; 424/487; 436/176

[56] References Cited

U.S. PATENT DOCUMENTS

| | | | |
|---|---|---|---|
| 4,238,480 | 12/1980 | Sawyer | 435/177 |
| 4,579,730 | 4/1986 | Kidron et al. | 514/3 |
| 4,795,436 | 1/1989 | Robinson | 424/422 |
| 4,849,227 | 7/1989 | Cho | 424/498 |
| 5,049,545 | 9/1991 | Löbermann et al. | 514/3 |
| 5,206,219 | 4/1993 | Desai | 514/3 |
| 5,340,731 | 8/1994 | Kilburn et al. | 435/179 |
| 5,438,040 | 8/1995 | Ekwuribe | 514/3 |
| 5,563,056 | 10/1996 | Swan et al. | 435/180 |

FOREIGN PATENT DOCUMENTS 1404513  6/1988  U.S.S.R. .

OTHER PUBLICATIONS

"Thermally Reversible Hydrogels Containing Biologically Active Species", Hoffman, Polymers in Medicine III, Elsevier Science Publishers B.V., Amsterdam, 1988, pp. 161–167.

"The Acetylation of Insulin", Lindsay et al, Biochem. J. 121 (1971), p. 737.

"Monosubstituted 2,2-Dimethyl-3-Formyl-L-Thiazolidine-4-Carbonyl Insulins", Lindsay et al, Eur. J. Biochem. 15 (1970) p. 547.

"Intramolecular Cross-Linked Insulin", D.G. Lindsay, Mar. 1971, Febs Lett., vol. 21, No. 1, p. 105.

"Improvement of Large Intestinal Absorption of Insulin by Chemical Modification with Palmitic Acid in Rats", Hashizume et al, J. Pharm. Pharmacol. 1992, 44:557–558.

"Trials of Lipid Modification of Peptide Hormones for Intestinal Delivery", Muranishi et al, Journal of Controlled Release, 19 (1992), PP. 179–180.

"Hypoglycemic Effect of Intestinally Administered Monosaccharide-Modified Insulin Derivatives in Rats", Haga et al, Chem. Pharm. Bull. 39(7) (1990), pp. 1983 & 1986.

"Effect of Trypsin Inhibitor on Passage of Insulin Across the Intestinal Barrier", Science, 127, 1988, pp. 1115–1116.

Seals, J.R. Evidence That Insulin Activates an Intrinsic Plasma Membrane. J. Biol. Chem. Jul. 25, 1980. vol. 255, No. 14, pp. 6529–6531.

Braganza, V.J. et al. Tryptase from Rat Skin. Biochemistry. 1991. vol. 30, No. 20, pp. 4997–5007.

Morishita, I. et al. Hypoglycemic Effect of Novel Oral Microspheres of Insulin. Int. J. Pharm. 1992 pp. 9–16.

Greenley, R.Z., et al. "Polymer Matrices for Oral Delivery". Polymer Preprints, vol. 31, No. 2 (Aug. 1990. Papers Presented at the Washington, D.C. Meeting, American Chemical Society, pp. 182–183.

Saffran, Murray, et al., "Biodegradable Azopolymer Coating . . ." Biochemical Society Transactions, vol. 18 (1990), pp. 752–754.

Damge, C., et al., "Nanocapsules as Carriers for Oral Peptide Delivery". Journal of Controlled Release, vol. 13 (1990), pp. 233–239.

Primary Examiner—Jeffrey E. Russel
Attorney, Agent, or Firm—Nestor W. Shust, Esq.

[57] ABSTRACT

An insulin-containing polymer composition intended for the oral administration of insulin, which comprises a hydrophilic polymer modified with an inhibitor of proteolytic enzyme, insulin and water, wherein the inhibitor of proteolytic enzymes is ovomucoid isolated from duck or turkey egg whites.

11 Claims, No Drawings

INSULIN-CONTAINING POLYMER COMPOSITION FOR ORAL ADMINISTRATION

TECHNICAL FIELD OF THE ART

The invention relates to polymer chemistry which is useful in the fields of medicine and biochemistry. More specifically, it is directed to polymer compositions for the oral delivery of insulin. Such compositions are therefore useful as medicinal preparations in treating diabetes.

BACKGROUND OF THE ART

Insulin is a polypeptide hormone having a molecular mass of about 6,000. It influences all kinds of metabolism in the organism: increases the penetration of glucose into living tissues, reduces the glycogen content in liver and increases its amount in muscles, increases protein synthesis intensity, etc.

The main method for administering insulin into an organism of a diabetic patient is by systematic subcutaneous and intramuscular injections. Being repeated hundreds and thousands of times, this procedure causes physical and emotional discomfort to a patient. The advantages of oral administration of insulin are so great and self evident that for many years attempts have been made to create insulin preparations which are resistant to the action of digestive proteinases and capable of penetrating blood through the mucosa of the intestines.

In tackling this problem, several approaches were proposed, including the modification of the insulin molecule itself, such as the replacement of the C-end residue of threonine with a more stable glycine residue; insulin molecule hydrophobization; preparation of monosaccharide derivatives or binding of insulin with other proteins. But despite the fact that in many cases modification per se brings about an increase in insulin resistance to the action of proteinases and prolongation of its effect on injection administration, no one was able to succeed in preparing hormone formulations which could be administered orally.

One of the possible approaches to solving this problem consists in jointly using insulin and compounds which increase the penetrability of the intestinal walls and facilitate the penetration of hormones into the blood stream. Compounds which are useful in this respect are, for example, fatty acid salts, surfactants, bile salts and chelate-forming compounds. The increased permeability of the intestinal walls contributes to the increase in the portion of the hormone reaching the blood stream in an active state, but only with the composition administered directly into the intestines, by-passing the gullet and the stomach. The administration of such compositions does not provide a therapeutic effect, even when high doses of insulin are used.

Quite natural seem to be attempts to use insulin in mixture with proteinase inhibitors which may protect insulin when administered into the intestines. A similar effect is observed in using compositions containing the proteinase inhibitors, insulin and compounds increasing the penetrability of intestinal walls.

More recently one of the most popular approaches to creating a form of insulin for oral delivery is putting the hormone inside a shell which protects it while it is passing through the digestive tract and then disintegrates in the small intestines, with active insulin being released. As such shells liposomes, hydrogels, nanocapsules or biodegradable polymers can be used.

Known in the art (U.S. Pat. No. 5,049,545 issued Sep. 17, 1991) are insulin-containing compositions for injections where insulin is immobilized in a polymer hydrogel. The polymers useful in such compositions are starch, dextran, polyoxyethylene, polyvinylpyrrolidone, cross-linked collagen, proteins and derivatives thereof, inclusive of the inhibitors of proteolytic enzymes. This results in the insulin-containing polymers displaying an increased resistance to the effect of blood proteolytic enzymes, a factor that provides an increased duration of the functioning of insulin in the bloodstream. However, the insulin-containing polymer compositions synthesized in this work do not show enough stability to the attack of the digestive enzymes which makes their oral use impossible.

Known (Saffran, M., Kumar, G. S., et al, Biochem. Soc. Trans. 1990, v. 18, N. 5, p. 752) are insulin-containing polymer compositions, that is, an insulin-containing gelatin capsule coated by a copolymer of styrene and hydroxyethylmethacrylate crosslinked with a divinylbenzene azo containing derivative. On oral use, the crosslinked copolymer is degraded under the action of the microorganisms of the intestines with the release of insulin penetrating the blood through the intestinal walls. A disadvantage of these compositions is a low resistance of synthesized composition to the action of digestive enzymes and hence a low activity of the insulin that penetrates the blood. With the oral administration of the above-mentioned crosslinked polymer into rats in an amount of from 1 to 40 mg. per rat (as calculated for insulin), the maximum reduction of glucose concentration in the animal blood was 25% on average (from 384 mg./100 ml. to 287 mg./100 ml.) and was observed 3–4 hours after the administration of the preparation.

Known (Damge, C., J. Controlled Release, 1990, V. 13, p. 233) are spherical nanocapsuled having a diameter of 250 to 350 nm on the basis of biodegradable polyisobutyl-2-cyanoacrylate containing insulin dispersed in a lipid phase. However, given the oral administration of nanocapsules, the noticeable reduction of glucose concentration (by 25%) is observed only in the case of very high insulin doses (by a factor of 100 U/kg.) and along with this the drug begins acting only 6 days after the capsules have been administered into the organism.

Closest to the claimed invention is a composition (Greenley, R. Z., Broun, T. M., et al, Polymer Prepr., 1990, v. 31, N 2, p. 182) representing insulin immobilized in a volume of a crosslinked polymer modified with the inhibitor of proteolytic enzymes. The crosslinked polymer is substantially a polyacrylic or polymethacrylic acid crosslinked with triethyleneglycoldi(meth)acrylate, and the inhibitor is represented by a protinin-protease inhibitor. A disadvantage of this composition is a low resistance of synthesized polymer hydrogels to the action of digestive enzymes giving cause to a low activity of blood-penetrating insulin. Thus, in the case of oral use of such a modified insulin composition to rabbits in the amounts corresponding to 50 units of insulin, the concentration of glucose in the blood is reduced in a matter of 30 min. from 380 to 360 mg./100 ml. and then 300 min. after administration of the preparation reaches 460 mg./100 ml. The peroral administration of a nonmodified hydrogel with no inhibitor (50 units of insulin) is accompanied by an approximate 23% reduction in the glucose concentration (from 310 to 240 mg./100 ml. after 300 min.). At the same time the subcutaneous injection of the rabbits with only 0.23 units of insulin leads to a reduction of said glucose concentration in blood from 330 to 120 mg./100 ml. (by 74%) 150 min. after the injection.

DISCLOSURE OF THE INVENTION

An object of the claimed invention is to increase resistance of insulin-containing polymer hydrogels to the effect of digestive enzymes so as to enable such preparations to be administered orally.

This object may be accomplished by employing an insulin-containing substantially crosslinked polymer hydrogel, modified by an inhibitor of proteolytic enzymes, in whose volume the insulin has been immobilized. The inhibitor of said proteolytic enzymes is an ovomucoid-enzyme isolated from the white of duck or turkey eggs (disclosed in USSR Inventor's Certificate N 1404513, issued Jan. 23, 1988).

Ovomucoid relates to the class of glycoproteins having a molecular mass of 31,000. The amino-acid composition of the protein part of ovomucoid is given in Table I. A molecule of ovomucoid comprises 12.5% by weight of glucosamine and 7.8% by weight of other sugars.

TABLE 1

Amino-Acid Content of Ovomucoid From the White of Duck Eggs

| Amino Acid | Residues per Molecule* | Amino Acid | Residues per Molecule |
|---|---|---|---|
| Asp | 30.14 (30) | Leu | 12.76 (13) |
| Thr | 17.98 (18) | Tyr | 9.53 (10) |
| Ser | 12.98 (13) | Phe | 5.00 (5) |
| Glu | 23.63 (24) | Lys | 16.36 (16) |
| Pro | 10.24 (10) | His | 4.23 (4) |
| Gly | 19.75 (20) | Arg | 1.95 (2) |
| Ala | 10.45 (10) | Trp | 0 |
| ½ Cys | 13.56 (14) | | |
| Val | 14.77 (15) | | |
| Met | 6.32 (6) | | |
| Ile | 3.59 (4) | TOTAL $M_r$ Residues | 212 25,178.0 |

To insulate the ovomucoid, 100 g. of the egg white is loaded into a flask provided with a stirrer. Thereafter a mixture of 70 g. of ethyl alcohol and 30 g. of the solution of 2.7 g. trichloracetic acid in 27.3 g. of distilled water (a total of 100 g. of solution) is added to the flask under stirring, at a rate of from 3 to 5 ml./min. Upon addition of the entire amount of the mixture the reaction mass is further stirred for 40 min. at a temperature of between 15° and 25° C. The precipitate is filtered off and rejected. The filtrate is transferred into a flask and 550 g. of ethyl alcohol is added thereto. The precipitate is dialyzed as the distilled water and the resulting solution is dried lyophylically. The yield: 0.8 g. of ovomucoid.

The polymer hydrogels are polymers swollen in water, said polymers being selected from homo- and copolymers based on acrylic and methacrylic acids, acrylamide, methacrylamide, hydroxyethylmethacrylate, vinylpyrrolidone.

The insulin used can be any natural or synthetic insulins.

The composition is prepared in the following manner: 0.01–1.0 g. of a pre-dried cross-linked polymer modified with 0.2–25 mg. of ovomucoid is placed in a 1 ml. insulin aqueous solution with a concentration of 0.01 to 3 mg./ml. (insulin activity is 25 U/ml.) for 1 hr. at room temperature during which time the polymer swells completely and is ready for use.

The amount of ovomucoid incorporated in a polymer hydrogel is determined by the fact that if said ovomucoid is used in an amount of less than 0.2 mg. for 1 ml. of gel, the ovomucoid does not perform the protective function and the insulin is destroyed by the proteolytic enzymes. The use of ovomucoid in an amount of above 25 mg. for 1 ml. of gel is unadvisable because this amount is already sufficient for the protection of any usable therapeutic insulin doses.

EXAMPLE 1

0.1 g. of a pre-dried crosslinked polyacrylamide, modified with ovomucoid, is placed in 1 ml. of an aqueous solution of insulin (insulin activity is 25 U/mg.) with a concentration of 1.0 mg./ml. per hour at room temperature. During this time limit the polymer swells completely and is ready to use. The synthesized hydrogel in an amount corresponding to 5 units of insulin per kg. of animal weight is administered to rabbits orally, using a catheter. Blood samples are collected after 30, 60, 90 and 120 minutes. The results are given in Table 2.

EXAMPLES 2–10

The procedure is conducted according to Example 1 using various crosslinked modified polymers, various concentrations of the insulin solution, various quantities of the cross-linked modified polymers and various amounts of ovomucoid. The formation and properties of the resulting hydrogels are given in Table 2.

EXAMPLE 11

(Control)

The procedure is conducted according to Example 1 but using a nonmodified polyacrylamide hydrogel. The results are given in Table 2.

EXAMPLES 12–13

Experimental diabetes is obtained (induced) in white rats of Water line, weighing 180 g., by way of intraperitoneally administered streptozotocin in the amount of 70 mg. for 1 kg. of weight. Synthesized polymers began to be introduced after the glucose level has exceeded 400 mg. %. The results are given in Table 2.

EXAMPLE 14

(Control)

The procedure is conducted according to Example 12 with an equal amount of insulin administered subcutaneously in the form of solution. The results are given in Table 2.

EXAMPLES 15–17

(Control)

Rabbits are treated orally with an insulin solution in an amount of 7 U/kg. of animal weight, a mixture of ovomucoid (2.5 mg./kg. weight) and insulin (8 U/kg) or a modified hydrogel (200 mg./kg. weight). The results are given in Table 2.

TABLE 2

| Ex. No. | Conditions of Obtaining a Hydrogel and Method for Using Same | | | | | Glucose Conc. in Blood Mg./100 ml. ± 8% | | | | |
|---|---|---|---|---|---|---|---|---|---|---|
| | Insulin Sol. Conc. mg./ml. | Modified polymer, g. per ml. insulin solution | Ovomucoid mg. per ml. of gel | Animal Type and Method of Application | | Time After Administration Minutes | | | | |
| | | | | | | 0 | 30 | 60 | 90 | 120 |
| 1 | 1.0 | PAA, 0.1 | 8.0 | Rabbit-Orally | | 150 | 132 | 110 | 80 | 80 |
| 2 | 3.0 | PAA, 0.05 | 7.7 | Rabbit-Orally | | 150 | 110 | 95 | 90 | 80 |
| 3 | 1.0 | PAA, 0.01 | 0.2 | Rabbit-Orally | | 140 | 100 | 95 | 90 | 80 |
| 4 | 5.0 | PAA, 0.1 | 25.0 | Rabbit-Orally | | 120 | 90 | 80 | 80 | 90 |
| 5 | 0.01 | PMA, 0.1 | 13.1 | Rabbit-Orally | | 160 | 125 | 95 | 90 | 120 |
| 6 | 0.05 | PHEMA, 1.0 | 3.8 | Rabbit-Orally | | 120 | 110 | 90 | 90 | 110 |
| 7 | 0.08 | PVP, 0.3 | 8.1 | Rabbit-Orally | | 110 | 90 | 70 | 90 | 90 |
| 8 | 3.0 | PAA, 0.1 | 7.4 | Rabbit-Orally | | 160 | 145 | 100 | 90 | 100 |
| 9*** | 1.0 | PAA, 0.2 | 7.4 | Rabbit-Orally | | 140 | 110 | 90 | 90 | 110 |
| 10 | 2.0 | PAA, 0.3 | 7.4 | Rabbit-Orally | | 120 | 90 | 80 | 80 | 90 |
| 11k | 1.0 | PAA-NM, 0.1 | | Rabbit-Orally | | 160 | 160 | 158 | 160 | |
| 12 | 1.0 | PAA, 0.1 | 7.4 | Rat-Orally | | 500 | 300 | 250 | 250 | |
| 13 | 3.0 | PAA, 0.1 | 0.1 | Rat-Orally | | 800 | 450 | 450 | 500 | |
| 14k | Insulin Solution | | | Rat-p.e. | | 400 | 160 | 145 | 150 | |
| 15k | Insulin Solution | | | Rabbit-Orally | | 152 | 151 | 150 | 160 | |
| 16k | Mixture of Ovomucoid and Insulin | | | Rabbit-Orally | | 154 | 154 | 155 | 153 | |
| 17k | Modified PAA | | | Rabbit-Orally | | 153 | 152 | 154 | 154 | |
| 18 | (Prototype) | | | Rabbit-Orally | | 380 | 360 | 430 | 410 | 420 |

Table Notations:
PAA-polyacrylamide
PAAC-polyacrylic acid
PMA-polymethacrylamide
PVP-polyvinylpyrrolidone
PHEMA-polyhydroxyethylmethacrylate
NM-non-modified
p.e.-subcutaneously
***In this experiment ovomucoid is taken from turkey eggs: in the balance (rest of the examples)-from duck eggs.
Insulin Used:
In Examples 1, 4, 10, 11, 12, 13, 14, 15, 16: porcine insulin;
In Examples 2, 3-cattle insulin;
In Examples 5-9-human insulin.

It is clearly seen from the data presented that the claimed compositions differ from those previously known because the chemical nature of the compositions used herein display an ability of preventing the insulin hydrolysis in the gastrointestinal tract and provides penetration of insulin into the bloodstream. Insulin activity in the case of the claimed compositions being used orally averages 60 to 70% of the activity of initial insulin when injected.

We claim:

1. A method of administering insulin comprising administering orally a composition which contains a polymer hydrogel that is swollen with water and insulin, said polymer having been modified with ovomucoid prior to swelling.

2. A method of claim 1, wherein the ovomucoid is in the amount of from 0.2 to 25 mg. per 0.01 to 1 g. of dry polymer.

3. A method of claim 2, wherein said ovomucoid is selected from the group consisting of duck and turkey ovomucoid.

4. A method of claim 3, wherein the polymer hydrogel is based on acrylamide and the ovomucoid is isolated from the white of duck eggs.

5. An insulin-containing polymer composition for oral administration of insulin, comprising a crosslinked hydrophilic polymer which is first modified with an inhibitor of proteolytic enzymes, wherein the inhibitor of proteolytic enzymes represents ovomucoid, and thereafter said modified hydrophilic polymer is swelled with an aqueous solution of insulin.

6. A composition of claim 5, wherein the crosslinked hydrophilic polymer is a hydrogel selected from the group consisting of homo- and copolymers based on acrylic and methacrylic acids, acrylamide, methacrylamide, hydroxyethylmethacrylate and vinyl-pyrrolidone.

7. A composition of claim 6, wherein the concentration of an ovomucoid in the crosslinked polymer is 0.2–25 mg/g hydrogel.

8. A composition of claim 6, wherein said composition contains 0.01 to 3 mg of insulin.

9. A composition of claim 5, wherein the ovomucoid is isolated from the white of duck or turkey eggs.

10. A composition of claim 5, wherein the ovomucoid is isolated from the white of duck eggs.

11. A composition of claim 7, wherein the hydrophilic polymer is based on acrylamide and ovomucoid is isolated from the white of duck eggs.

* * * * *